US00PP18080P2

(12) United States Plant Patent
Waldvogel

(10) Patent No.: US PP18,080 P2
(45) Date of Patent: Sep. 25, 2007

(54) ***EUONYMUS* PLANT NAMED 'WALDBOLWI'**

(50) Latin Name: *Euonymus fortunei*
Varietal Denomination: Waldbolwi

(75) Inventor: Karel Waldvogel, Putten (NL)

(73) Assignee: Spring Meadow Nursery, Inc., Grand Haven, MI (US)

( * ) Notice: Subject to any disclaimer, the term of this patent is extended or adjusted under 35 U.S.C. 154(b) by 38 days.

(21) Appl. No.: 11/188,965

(22) Filed: Jul. 25, 2005

(51) Int. Cl.
*A01H 5/00* (2006.01)

(52) U.S. Cl. ..... Plt./246
(58) Field of Classification Search ..... Plt./246
See application file for complete search history.

(56) References Cited

PUBLICATIONS

Upov CD–ROM Plant Variety Database 2006/01 search cultivar Waldbolwi.*

* cited by examiner

*Primary Examiner*—Kent Bell
*Assistant Examiner*—Annette H Para
(74) *Attorney, Agent, or Firm*—C. A. Whealy

(57) ABSTRACT

A new and distinct cultivar of *Euonymus* plant named 'Waldbolwi', characterized by its compact and upright plant habit; freely basally branching growth habit; distinct yellow-colored stems and leaves; and stems and leaves resist sunburning.

1 Drawing Sheet

Botanical designation: *Euonymus fortunei.*
Cultivar denomination: 'Waldbolwi'.

BACKGROUND OF THE INVENTION

The present Invention relates to a new and distinct cultivar of *Euonymus* plant, botanically known as *Euonymus fortunei,* and hereinafter referred to by the name 'Waldbolwi'.

The new *Euonymus* is a naturally-occurring branch mutation of the *Euonymus fortunei* cultivar Emerald 'n Gold, not patented. The new *Euonymus* was discovered and selected by the Inventor in a controlled environment in Henstedt-Ulzburg, Germany in April, 2000. The new *Euonymus* was selected on the basis of its unique leaf coloration.

Asexual reproduction of the new cultivar by cuttings since May, 2000 in Henstedt-Ulzburg, Germany, has shown that the unique features of this new *Euonymus* are stable and reproduced true to type in successive generations.

SUMMARY OF THE INVENTION

Plants of the cultivar Waldbolwi have not been observed under all possible environmental conditions. The phenotype may vary somewhat with variations in environment such as temperature and light intensity without, however, any variance in genotype.

The following traits have been repeatedly observed and are determined to be the unique characteristics of 'Waldbolwi'. These characteristics in combination distinguish 'Waldbolwi' as a new and distinct *Euonymus* cultivar:

1. Compact and upright plant habit.
2. Freely basally branching growth habit.
3. Distinct yellow-colored stems and leaves.
4. Stems and leaves resist sunburning.

Plants of the new *Euonymus* are most similar to plants of the parent, the cultivar Emerald 'n Gold. In side-by-side comparisons conducted in Putten, The Netherlands, plants of the new *Euonymus* differed from plants of the cultivar Emerald 'n Gold in the following characteristics:

1. Plants of the new *Euonymus* and the cultivar Emerald 'n Gold differed in stem coloration as plants of the cultivar Emerald 'n Gold have green-colored stems.
2. Plants of the new *Euonymus* and the cultivar Emerald 'n Gold differed in leaf coloration as plants of the cultivar Emerald 'n Gold have green and yellow variegated leaves.

Plants of the new *Euonymus* can be compared to plants of the *Euonymus* cultivars Emerald Gaitey, not patented; Coloratus, not patented; and Interbolwi, disclosed in U.S. Plant Pat. No. 10,424. In side-by-side comparisons conducted in Putten, The Netherlands, plants of the new *Euonymus* differed from plants of the cultivars Emerald Gaitey, Coloratus and Interbolwi in the following characteristics:

1. Plants of the new *Euonymus* and the cultivars Emerald Gaitey, Coloratus and Interbolwi differed in stem coloration as plants of the cultivars Emerald Gaitey, Coloratus and Interbolwi have green-colored stems.
2. Plants of the new *Euonymus* and the cultivars Emerald Gaitey, Coloratus and Interbolwi differed in leaf coloration as plants of the cultivars Emerald Gaitey, Coloratus and Interbolwi have green and yellow variegated leaves.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the actual colors of the new *Euonymus*. The photograph comprises a side perspective view of a typical plant of 'Waldbolwi' grown in a container.

DETAILED BOTANICAL DESCRIPTION

Plants shown in the aforementioned photograph and used in the following description were grown in containers under conditions which closely approximate commercial production conditions in a glass-covered greenhouse in Putten, The Netherlands. Plants in the photograph and those used for the description were about 1.5 years old when the photograph and description were taken. During the production of the plants, day temperatures ranged from 0° C. to 38° C. and night temperatures ranged from 0° C. to 18° C. In the following description, color references are made to The Royal Horticultural Society Colour Chart, 1995 Edition, except where general terms of ordinary dictionary significance are used.

Botanical classification: *Euonymus fortunei* cultivar Waldbolwi.

Parentage: Naturally-occurring branch mutation of the *Euonymus fortunei* cultivar Emerald 'n Gold, not patented.

Propagation:

*Type.*—By cuttings.

*Time to initiate rooting, summer.*—About 25 days at 20° C.

*Time to initiate rooting, winter.*—About 40 days at 12° C.

*Time to produce a rooted young plant, summer.*—About four months at 20° C.

*Time to produce a rooted young plant, winter.*—About five months at 14° C.

*Root description.*—Moderately thick; creamy white in color.

*Rooting habit.*—Freely branching; dense.

Plant description:

*Plant and growth habit.*—Perennial. Compact and upright plant habit. Freely basal branching habit; about two to three lateral branch per basal branch; dense and bushy plant habit.

*Plant height.*—About 18 cm.

*Plant width.*—About 17 cm.

*Lateral branch description.*—Length: About 4 cm. Diameter: About 3 mm. Internode length: About 1.2 to 2.2 cm. Strength: Strong. Texture: Smooth, glabrous. Color: 151D overlain with 8C; towards the base, 138A.

*Foliage description.*—Arrangement: Opposite, simple. Length: About 1.8 cm. Width: About 1.3 cm. Shape: Lanceolate. Apex: Acute. Base: Cuneate. Margin: Crenate. Texture, upper and lower surfaces: Smooth, glabrous. Venation pattern: Pinnate. Color: Developing foliage, upper surface: 151B; venation, 145D. Developing foliage, lower surface: 145C; venation, 145C. Fully expanded foliage, upper surface: 13B to 13C; venation, 10D. Fall color of the foliage: close to 53A. Fully expanded foliage, lower surface: 11B; venation, 11B. Petiole length: About 2 mm. Petiole diameter: About 1 mm. Petiole texture, upper and lower surfaces: Smooth, glabrous. Petiole color, upper and lower surfaces: 10D.

Flower description: Flower development on plants of the new *Euonymus* has not been observed.

Disease/pest resistance: Plants of the new *Euonymus* have not been noted to be resistant to pathogens and pests common to *Euonymus*.

Temperature tolerance: Plants of the new *Euonymus* have been observed to tolerate temperatures from about −15° C. to about 30° C.

It is claimed:

1. A new and distinct cultivar of *Euonymus* plant named 'Waldbolwi', as illustrated and described.

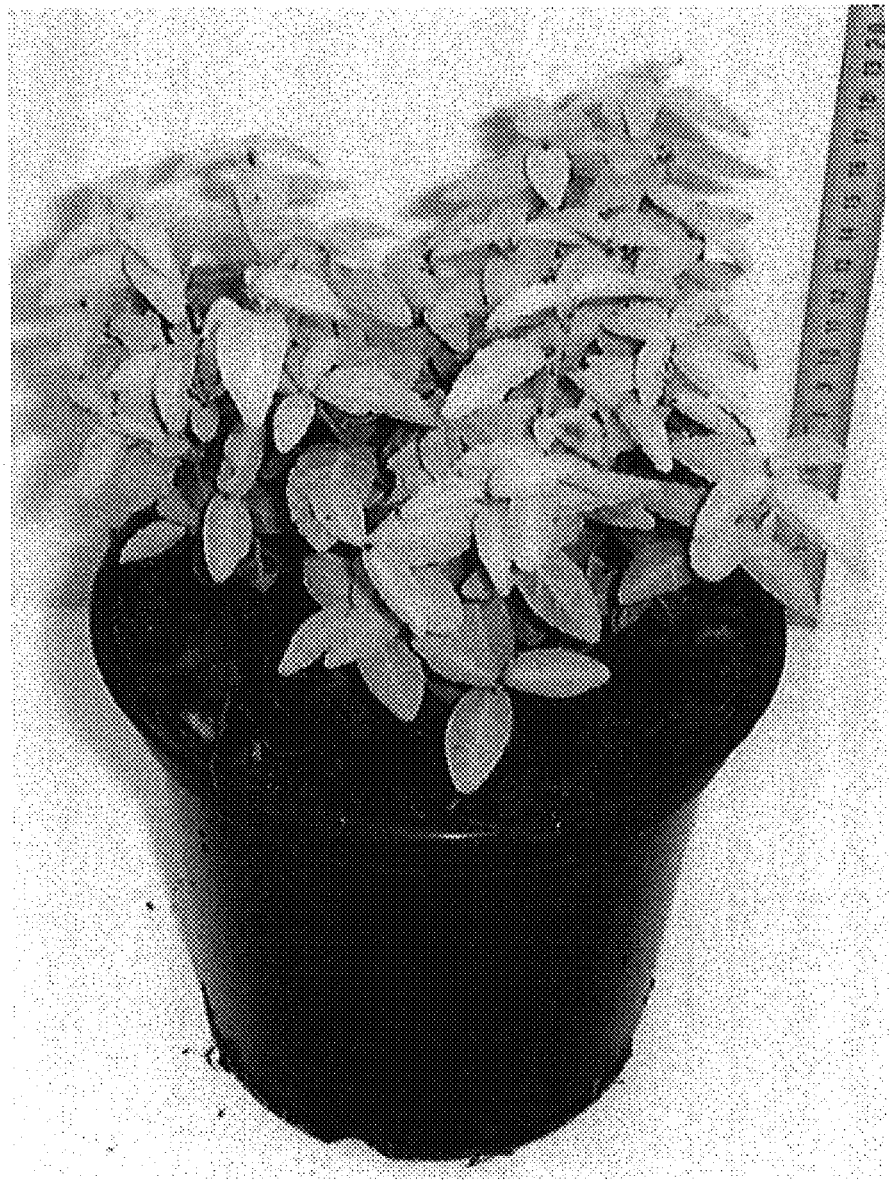

* * * * *